Figure 1:
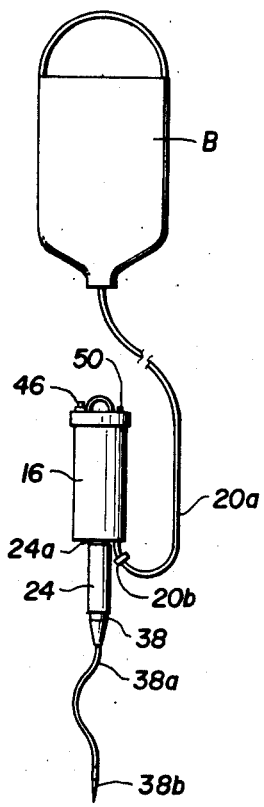

United States Patent [19]

Howell

[11] 4,243,032

[45] Jan. 6, 1981

[54] PARENTERAL FLUID ADMINISTRATION SETS

[76] Inventor: William L. Howell, 3615 Macomb St., NW., Washington, D.C. 20016

[21] Appl. No.: 3,923

[22] Filed: Jan. 16, 1979

[51] Int. Cl.³ .............................................. A61M 5/16
[52] U.S. Cl. ................................................ 128/214 C
[58] Field of Search ............ 128/214 R, 214 C, 214.2, 128/227, 228; 222/416; 137/129, 131, 135, 142, 399

[56] References Cited

U.S. PATENT DOCUMENTS

| | | | |
|---|---|---|---|
| 2,090,273 | 8/1937 | Wagner | 137/399 |
| 2,640,358 | 6/1953 | McClure et al. | 128/416 X |
| 3,949,745 | 4/1976 | Howell | 128/214 C |
| 3,965,895 | 6/1976 | Dabney | 128/214 C |
| 4,099,527 | 7/1978 | Howell | 128/214 C |

FOREIGN PATENT DOCUMENTS 21724  9/1947  Finland ........................... 137/135

Primary Examiner—Dalton L. Truluck

[57] ABSTRACT

A floating siphon-type regulator for incorporation in parenteral fluid administration sets and which is characterized by a design enabling a simplified, fast start-up procedure and which incorporates a simple, effective means for increasing or decreasing flow rates as called for by the viscosity of the particular solution being administered.

8 Claims, 5 Drawing Figures

U.S. Patent  Jan. 6, 1981  4,243,032

PARENTERAL FLUID ADMINISTRATION SETS

THE INVENTION—GENERAL STATEMENT

This invention relates to improvements in parenteral solution administration sets generally and more particularly to an improved floating siphon-type flow regulator for incorporation in such administration sets.

BACKGROUND OF THE INVENTION

While my prior U.S. Pat. No. 3,949,745 dated Apr. 13, 1976 and U.S. Pat. No. 4,099,527 dated July 11, 1978 disclose and claim novel floating siphon-type regulators for incorporation in parenteral fluid administration sets which were earlier evaluated by persons qualified to judge same to represent an advance in the art, such have not been accorded commercial status, due to alleged complexity in their respective start-up procedures; because of their alleged ability to provide a constant flow rate in but a limited range of application; and/or further because they failed to take into account the fact that solution viscosity differences which reflect themselves in the differing weights of the various solutions being used can affect the absolute rate of flow and hence of delivery of the fluid to the needle.

OBJECTS OF THE HEREIN INVENTION

Among the objects of improved regulator according to the present invention may be noted the provision of an improved floating siphon-type flow regulator for parenteral fluid administration sets which is characterized by structure and a mode of operation rendering such sets well suited for routine floor use by hospital personnel; the provision of a flow regulator for use as aforesaid characterized by a simplified, fast start-up procedure; the provision of a flow regulator for use as aforesaid which is so constituted as to permit increase or decrease of flow rates as called for; and the provision of a flow regulator for use as aforesaid enabling differences in the viscosity of the solution being or about to be administered to be compensated for to a degree providing a substantially constant (absolute) rate of fluid delivery to the needle.

Figure 4:
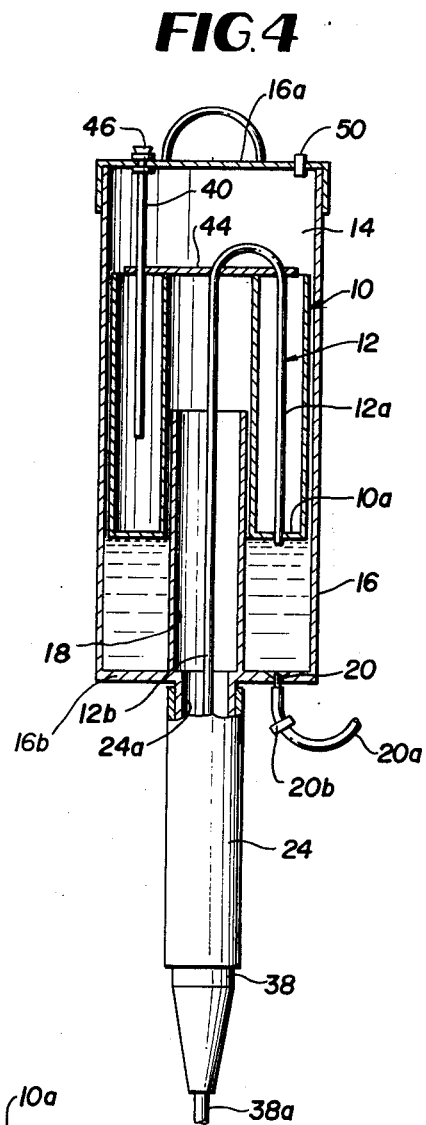
Figure 2:
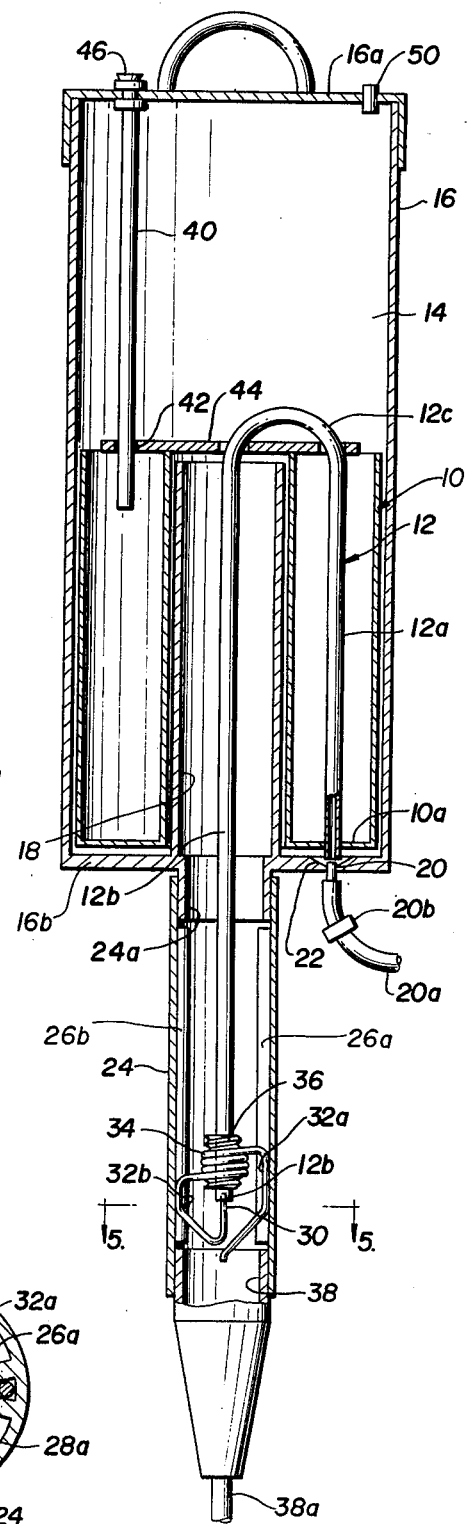
Figure 3:
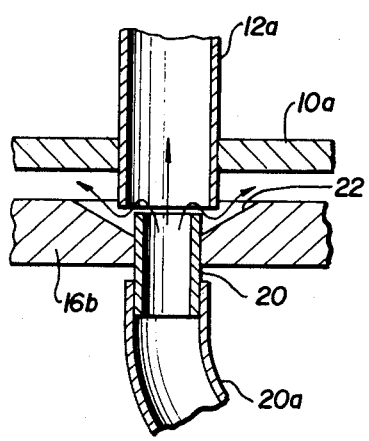
Figure 5:
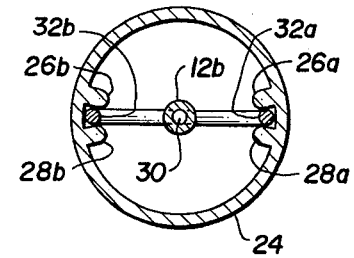

The above and other objects of the present invention will be pointed out in or will become apparent from a consideration of the appended illustrative drawing figures and accompanying description thereof, wherein FIG. 1 is a view in elevation of a parenteral fluid administration set incorporating a flow regulator according to the invention;

FIG. 2 is a view in elevation, with certain of its parts shown in section, of a preferred form of improved floating siphon-type flow regulator according to the present invention showing parts thereof in readiness for a start-up procedure;

FIG. 3 is an enlarged detail view of the means provided according to the present invention for jetting fluid from a high-level source directly into the U-tube of the floating siphon assembly, as is herein proposed, and substantially simultaneously therewith for supplying fluid to the regulator chamber on which the float thereof may ride; and FIG. 4 is a view in elevation similar to FIG. 2, but illustrating the floating siphon assembly in one of the various elevated positions which it may assume, depending on the particular level of the fluid present in the regulator chamber; and FIG. 5 is a transverse section taken on plane 5—5 of FIG. 2.

Referring to the aforesaid drawing figures, it will become apparent therefrom that the herein regulator embodies certain structural features of the floating siphon-type regulators according to one or both of my aforementioned U.S. Pat. Nos. 3,949,745 and 4,099,527. More particularly, the herein regulator employs a floating siphon-type assembly comprising a float member 10 and a siphon U-tube 12 affixed thereto for movement in unison therewith within an upright cylindrical chamber 14 formed by a cylindrical, preferably clear-plastic shell-form member 16 closed at its upper end by an end cap 16a, and at its lower end preferably by a relatively thick, rigid bottom plate 16b, which latter mounts an open-ended upright tube 18 extending upwardly-axially into the chamber 14 and serving as an overflow tube.

The float member 10 of the float U-tube assembly preferably takes the form of an open-top annular cup, in whose central aperture the upright overflow tube 18 is accommodated, such arrangement serving to center the float in its vertical movement in accordance with variations in the level of the fluid then present in the chamber on which said float member rides. And as will hereinafter become apparent, the cup interior space accommodates both the shorter arm of the siphon U-tube and the rod means serving to prevent any turning movement of the float U-tube assembly about the vertical axis of said chamber, whereby said shorter arm of the U-tube is constrained to move in a substantially unvarying vertical path responsive to variations in the level of fluid in said chamber, which latter is an important feature of the invention to be described.

Now describing features novel to the herein regulator, the aforesaid siphon U-tube of the float-siphon assembly and which comprises a shorter arm 12a and a longer arm 12b connected by a U-bend 12c, is preferably fashioned of conductive metal so as not to take a charge as tubes of plastic material have been known to do. Also, said shorter arm is affixed to the bottom-end wall 10a of the float member, in position such that its bore end projects slightly through and terminates below said float bottom wall, and, more importantly, is disposed in substantially exact axial alignment with the upper open end of a short-length rigid open-ended pipe 20 which extends upwardly for a short distance through the relatively thick regulator bottom-end plate 16b, and terminates in and opens into a funnel-shaped aperture 22 in said end plate, into which aperture the bore end of the shorter siphon arm 12a also initially extends.

The outer (lower) end of said aforesaid short-length pipe 20 connects to a tubing line 20a extending to and being connected into a source of the fluid to be administered, illustratively a hang-up bag or bottle B, which initially is maintained at a substantially higher elevation than the regulator proper, but which may be lowered after start-up to maintain a particular level of fluid in the regulator chamber. A manually closed clamp valve 20b disposed just downstream (ahead) of its connection with the aforesaid pipe 20 controls flow of the fluid from said bag or bottle source thereof through the tubing line 20a to said pipe 20 from which, assuming manual actuation of the clamp valve to open position, fluid under the substantial head thereof in the high-level source and adjacent length portion of the tubing line, will issue in the form of an upwardly flowing jet directly into and upwardly through the funnel-shaped aperture 22 which in turn directs the fluid jet or a substantial portion thereof into the open-ended bore of the shorter arm 12a of the U-tube, thereupon filling same throughout its full length and exiting from the open end of the longer arm 12b in the controlled manner to be described.

Reverting to the aforesaid aperture 22, its funnel shaping results also in fluid flowing (leaking) generally radially outwardly relative to the lower-end of the siphon arm 12a. That is to say, the aforesaid arrangement provides a leak-permitting connection between the upper end of the pipe 20 and the interior space of the regulator, with the fluid leaking therethrough as is illustrated in FIG. 3 proceeding to build up a body of fluid in the regulator chamber to a level or levels enabling the float 10 and connected U-tube 12 to float thereon. Thus, it will be appreciated that according to the invention, means are provided for substantially simultaneously supplying fluid directly to and through the siphon-tube bore and to the interior of the regulator chamber as well; that said means is disposed downstream of the regulator; and that it supplies the fluid as aforesaid in the form of an upwardly directed jet.

As in my prior patents aforesaid, the longer arm 12b of the U-tube 12 extends axially downwardly through the aforesaid open-ended upright overflow tube 18, but rather than terminating within an elongate drip chamber as was heretofore more or less conventional, instead terminates within a cylindrical, manually turnable needle-valve housing 24 swively (rotably) connected to a fixed short-length tubular nipple 24a depending from the regulator bottom-end plate 16b, being preferably formed integral with said end plate.

By reference to FIG. 5, the inside wall surface of said cylindrical housing 24 is provided with two pairs of oppositely disposed ribs or rib-forming means 26a, 28a and 26b and 28b, adjacent ribs of the pairs thereof being spaced apart circumferentially so as to provide grooves for the reception of oppositely disposed wing portions of the needle-valve assembly now to be described and which is best illustrated by FIG. 2.

More particularly, said needle-valve assembly is preferably fashioned from a single-length of stiff shape-retaining wire bent to provide a straight-length needle portion 30 extending on the axis of the longer arm 12b of the U-tube and being disposed so that its upper end is adapted to be projected toward and into the bore of said longer arm and retracted therefrom when actuated to do so, with the degree of its projection toward and into and from said bore determining the rate of fluid flow therefrom. In addition to said needle portion 30, said wire is bent to form two side wing portions 32a, 32b which extend radially outwardly and seat in the grooves between the aforesaid rib formations 26a, 28a and 26b, 28b; and a cross-length portion extending transversely between and connecting said wing portions and which intermediate its ends is coiled to provide a helical thread formation functioning as a nut 34 whose coils threadedly engage with threads provided on the external cylindrical surface of a short axial length sleeve 36 fast on the end-length portion of the said longer siphon-tube arm 12b.

By the aforesaid arrangement, manual rotation of the rotatable housing 24 in one or the opposite directions, as by simple rotative finger pressures thereon, effects axial translation of the needle-valve assembly as a unit in direction as to project the upper end of the needle 30 proper toward, into or from the end of the bore of the tube 12b.

Preferably, the arrangement is further such that two full turns of the sleeve-form housing will fully open up said bore, with gradual to full closing being effected by controlled rotation of said housing in the opposite or valve-closing direction. By proper shaping of the end portion of the needle it is also possible to achieve known rates of flow with particular housing-angle settings, i.e., a calibrated rate of flow.

A further feature of note is that the lower end of the manually rotatable housing is swivelly connected to a non-rotatable sleeve 38, to which the conventional tubing line 38a to an intravenous needle 38b is connected. By providing such latter swivelling connection, snarling of the tubing line 38a is prevented when the sleeve-form housing 24 is rotated.

According to a further novel feature of the herein improved flow regulator, means are provided to insure against the float component 10 and thereby the float U-tube assembly 10, 12 considered as a unit, turning or being turned accidently about its axis as it rises and lowers in response to variation in the level of the fluid present in the regulator chamber, said means thus serving to maintain the short arm 12a of the U-tube in exact vertical alignment with the pipe 20 through which fluid from the high level source is jetted into the bore of said shorter arm. More particularly, said means preferably comprises a rigid, stationarily mounted, small-diameter rod 40 affixed adjacent its upper end in the regulator top-end cap 16a to extend downwardly therefrom into the regulator chamber, said rod having length such that it projects through an aperture 42 in a cross-strap 44 affixed to and extending slightly beyond the top edges of the inner walls of the float cup and spanning the top opening of the upright overflow tube 18. Thus, the annular float and U-tube assembly is constrained to move vertically, i.e., against turning motion, as it changes elevation in response to variations in fluid level in the regulator chamber.

To insure against float and U-tube motion in response to fluid level variations being impeded as by an airlock, a two-way air vent valve 50 is carried by the regulator, being preferably mounted to the regulator top-end cap 16a. Such prevents air pressure within the regulator chamber to build up to a point affecting free float motion therein.

Without further description, it will be appreciated that the herein regulator provides a simplified, fast start-up procedure and also adds highly effective means for altering siphon flow rates as desired or required. More in detail, by introducing fluid in the form of a jet into the regulator chamber downstream of and directly upwardly into the bore of the shorter siphon arm, fluid flow through the siphon tube is greatly accelerated, a feature which assures fast startup. It is also a feature of the herein fluid-supply means that it functions to supply fluid to the siphon bore and to the regulator chamber substantially simultaneously, without in any way affecting the fast start-up procedure. Further, the invention provides simple yet highly effective needle-valve means associated with the end of the longer siphon arm for varying the rate of flow from the siphon U-tube merely by turning by finger pressure a freely rotatable cylindrical needle-valve housing interposed in the delivery end of the regulator.

Finally, it will be appreciated that the mode of operating the herein regulator is fool-proof as well as simple, thus rendering parenteral fluid administration sets in which my herein described regulators are incorporated well suited for routine floor use in hospitals, nursing homes, etc.

Having disclosed my improved regulator, its uses as aforesaid and its many advantages, I make the following claims therefor;

1. A floating siphon-type flow regulator for parenteral fluid administration sets incorporating a source of the fluid to be administered which is maintained at a high level relative to that of the regulator, said regulator comprising an upright, substantially cylindrical chamber-forming member closed at its ends by top and bottom end plates respectively, a float U-tube assembly comprising a float member and a siphon U-tube affixed to said float member, means preventing turning movement of said assembly about the axis of said chamber-forming member, whereby the shorter arm of the U-tube is constrained to move in an unvarying vertical path responsive to variations in the level of fluid present in the chamber-forming member, and means for introducing fluid from said source at a manually controllable rate to said member interior through the bottom end plate and at a point thereof which is vertically aligned with the bore of said shorter arm of the U-tube, being thereby effective to build up a body of the fluid on which said float U-tube assembly may float as a unit and simultaneously therewith to direct a portion of the so introduced fluid to and into the bore of the shorter U-tube arm.

2. A floating siphon-type flow regulator according to claim 1, wherein said means for introducing fluid as aforesaid is effective to introduce the fluid from a point downstream of the regulator proper and in the form of an upwardly directed jet into the bore of the shorter arm of the U-tube.

3. A floating siphon-type flow regulator according to claim 1, wherein said fluid-introducing means comprises an uprightly disposed, small diameter pipe affixed in and projecting into an aperture provided in the bottom end plate of the cylindrical-chamber forming member in position such that it is adapted to supply fluid from said pipe in the form of an upwardly directed jet into the bore of the U-tube, and said aperture is shaped as also to permit leakage flow of the fluid into the chamber space surrounding said aperture.

4. A floating siphon-type flow regulator according to claim 3, including means for maintaining the float U-tube assembly in position such that the open end of the shorter siphon arm is always vertically aligned with said upright pipe.

5. A floating siphon-type flow regulator according to claim 4, wherein the float component of said assembly has annular upright cup configuration and said means for maintaining the U-tube thereof in its aforesaid aligned position includes a strap member affixed to the top edges of and extending transversely across said float, rod means affixed to the top end closure-plate of and extending downwardly into the chamber interior, the free lower end of said rod means engaging the strap member in such manner as prevents turning motion of said float U-tube assembly while permitting said assembly to partake of vertical motion responsive to variations in liquid level in said chamber.

6. A Floating siphon-type flow regulator according to claim 1, wherein means for controlling the rate of the fluid passage through and from said tube bore are provided and comprises a needle-valve assembly associated with the end of the longer arm of the U-tube and being axially translatable by a manually turnable sleeve member.

7. A floating siphon-type flow regulator according to claim 6, wherein said sleeve member is turnably mounted on and depends from a nipple affixed to and depending from the bottom end plate of the regulator chamber.

8. A floating siphon-type flow regulator according to claim 7, wherein said needle-valve assembly is fashioned from a single length of stiff, form-retaining wire formed to provide a straight needle-valve portion disposed on the axis of the longer tube-arm bore, side wing portions extending radially outwardly therefrom and engaging in grooves between rib formations on the inner surface of said rotable sleeve member, and a cross portion connecting said side wing portions and being provided with a nut formation in its intermediate length portion, said nut providing threads meshing with threads provided on the lower end of said longer siphon arm.

* * * * *